United States Patent [19]
Eckhardt et al.

[11] Patent Number: 6,162,227
[45] Date of Patent: Dec. 19, 2000

[54] BONE CUTTER

[75] Inventors: Harald Eckhardt; Gero Krause, both of Stephanskirchen, Germany

[73] Assignee: Plus Endoprothetik AG, Rotkreuz, Switzerland

[21] Appl. No.: 09/254,117

[22] PCT Filed: Jun. 19, 1997

[86] PCT No.: PCT/EP97/03211

§ 371 Date: Apr. 29, 1999

§ 102(e) Date: Apr. 29, 1999

[87] PCT Pub. No.: WO98/08444

PCT Pub. Date: Mar. 5, 1998

[30] Foreign Application Priority Data

Aug. 26, 1996 [DE] Germany .......................... 196 34 484

[51] Int. Cl.[7] .................................................. A61B 17/16
[52] U.S. Cl. ................................ 606/84; 606/85; 407/30; 408/127
[58] Field of Search ............................... 606/84, 85, 180; 408/127; 407/29.13, 30

[56] References Cited

U.S. PATENT DOCUMENTS

| | | | |
|---|---|---|---|
| 2,753,618 | 7/1956 | Stanziale | 407/30 |
| 4,946,461 | 8/1990 | Fischer . | |
| 5,601,561 | 2/1997 | Terry et al. | 606/85 |

FOREIGN PATENT DOCUMENTS

| | | |
|---|---|---|
| 2437772 | 2/1976 | Germany . |
| 1227769 | 6/1972 | United Kingdom . |

*Primary Examiner*—Michael Buiz
*Assistant Examiner*—Julian W. Woo
*Attorney, Agent, or Firm*—Knobbe, Martens, Olson & Bear LLP

[57] ABSTRACT

A bone milling tool for precise preparation of bones includes a milling head connected to a driveshaft. The driveshaft simultaneously serves as a guide element which is guided in a bone. The bone milling tool further includes a toothing which is arranged on the milling head facing the driveshaft.

14 Claims, 2 Drawing Sheets

BONE CUTTER

FIELD OF THE INVENTION

The invention relates to a bone milling tool for precise preparation of.

BACKGROUND OF THE INVENTION

From the DE-OS 27 48 452 is known a bone milling tool for round milling a hip joint head which is provided with a central hole into which a centering pin is inserted. The milling head is joined to a driveshaft which is,. at least near the area of the milling head, of tubular design.

Also known is a bone milling tool as illustrated in FIG. 4. A bone milling tool of this type is used for precisely fitting preparation of bones, in particular tubular bones. It is important, in particular with cementfree implantation of prosthesis, to create an extremely precisely fitting bone bed to accommodate the prosthesis, on the one hand to ensure the largest possible contact surface for fast grafting of the bone and on the other hand to eliminate micro movements. Rotary instruments are preferred as the precision of oscillating saws is insufficient.

Bone milling tool 10a illustrated in FIG. 4 is a front-end milling tool. It is composed of a cylindrical milling head 12a with cutting teeth configured at the front. A guide pin 30 is also arranged at this side. A driveshaft 14' is mounted to the rear of milling head 12a. When using this bone milling tool 10a, guide pin 30 is pushed into a guide bore which has been entered into the bone, thus ensuring guided and directionally stable processing. Exerting pressure (see arrows 26 in FIG. 4) onto driveshaft 14' in the direction of guide pin 30 establishes contact of front-end cutting teeth with the bone and mills a rotary-symmetrical surface into the depth.

The problem with both of the aforedescribed bone milling tools lies with the respective driveshaft, which protrudes from the field of operation and has to be connected to a drive unit. If the field of operation is small and access has to be of narrow design for anatomical or surgical reasons, then it can happen that, whilst milling downwards, the driveshaft is forced out of its direction by protrusions in the field of operation, which results in a directionally unstable or directionally incorrect milling surface. The result is an inaccurate bone bed, both relative to the contact surface and relative to positioning of a prosthesis.

SUMMARY OF THE INVENTION

It is an object of the invention to create a bore milling tool which makes it easily possible to establish a bone bed of maximum fitting accuracy even in the event of a small field of operation.

An aspect of the invention involves a bone milling tool for precise preparation of bones. The bone milling tool includes a milling head connected to a driveshaft. The driveshaft simultaneously serves as a guide element which is guided in a bone. The bone milling tool further includes a toothing which is arranged on the milling head facing the driveshaft.

According to the invention, the driveshaft simultaneously serves as guide element and is passed through a continuous guide bore which is established in the bone. As the toothing is arranged at the side of the driveshaft on the milling head, work is, in contrast to conventional bone milling tools, no longer carried out by pushing but by pulling.

When using the bone milling tool, the driveshaft extends from the milling head in the direction of the bone and through the guide bore which has been established in the latter. The driveshaft then no longer protrudes from the field of operation and can no longer be forced out of its direction by objects which protrude into the field of operation. This ensures production of a bone bed of high fitting accuracy.

The driveshaft is preferably of flexible design. The use of a flexible driveshaft is only made possible because work is no longer carried out by pushing but by pulling.

According to a further advantageous embodiment, a guide pipe is inserted into the guide bore which has been established in the bone. The driveshaft then no longer rubs against the bone or adjacent soft parts. The guide pipe can be pushed thereinto from the end of the bore located opposite the field of operation. When lowering the milling work, the milling head pushes the guide pipe in front of it without milling it.

As the driveshaft has to be guided all the way through the bone, and as it has to be connected on one side to the milling head and on the other side to a drive unit, at Least one of these connections has to be of detachable design. The detachable connection is preferably provided at the point of transition from driveshaft to milling head or at the point of transition from driveshaft to drive unit.

In the first case, the driveshaft is prior to milling inserted from the opposite end of the guide bore in the direction of the field of operation and connected to the milling head. In the second case, the driveshaft is pushed from the field of operation through the guide bore and on exit from the bone on the opposite side connected to the drive unit.

The milling head can be of varying design, but should be rotary-symmetrical. For cylindrical milling, a milling head is chosen, the toothing of which is configured in one plane. This produces a plane cutting surface standing perpendicularly to the driveshaft. Alternatively, a milling head can be used which comprises a cutting surface which is concave, convex or a combination of such surfaces. This allows milling of spherical, conical, cylindrical, polygonal, wavy or any other rotary-symmetrical shape surfaces.

A preferred embodiment is characterised in that the cutting surface is extended by a non-cutting protective collar. The protectice collar keeps soft parts away from the milling zone.

The toothing of the milling head can be of conventional design, i.e. it can be milled or hammered. However, particularly advantageous is the use of a rasplike toothing with additional waste-removal holes provided in the milling head. This makes it possible to remove bone waste from the milling area.

A special combination of the latter embodiment of a toothing is established when a catching device, in particular a collecting vessel, is arranged at the rear of the milling head. For example, the use of a small basket or dishlike container in which occurring bone waste can be collected, would be useful. This can not only prevent pollution of the field of operation by such waste and reduce the danger of an induced undesirable ectopic bone growth, but additional waste collected in the container can be used further as valuable autologem spongiosa pulp.

BRIEF DESCRIPTION OF THE DRAWINGS

The invention will now be described in more detail, also in view of further advantages and features, based on exemplary embodiments and with reference to the enclosed drawings. The drawings show in FIG. 1 a diagrammatical side view of an exemplary embodiment of the inventive bone milling tool.

DETAILED DESCRIPTION OF THE INVENTION

Figure 1:
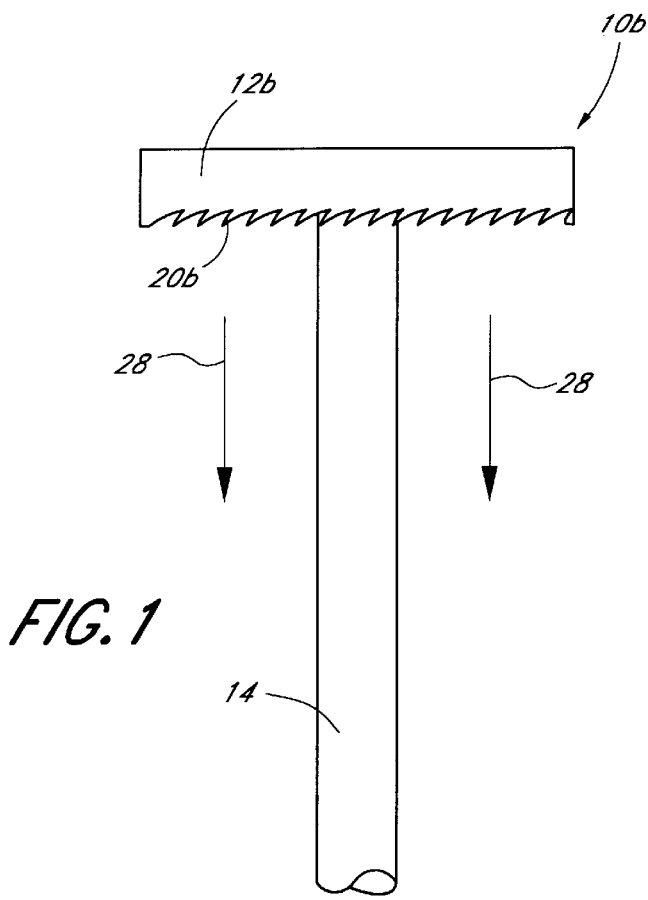

FIG. 1 illustrates an exemplary embodiment of a bone milling tool 10b, consisting essentially of a cylindrical milling head 12b and a driveshaft 14.

Milling head 12b has at its surface facing toward driveshaft 14 a toothing 20b which is, in the present exemplary embodiment, milled. However, it can also be hammered or arranged in a different manner. All teeth of toothing 20b lie essentially in one plane, so that its use produces a cutting surface which extends perpendicularly to driveshaft 14.

Figure 4:
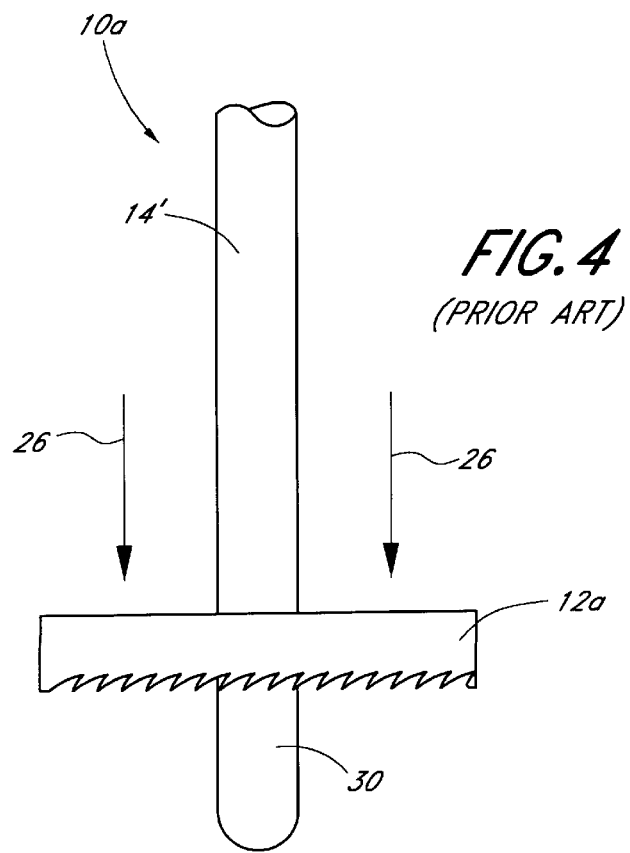
FIG. 4 a diagrammatical side view of a bone milling tool of the prior art.

Driveshaft 14 is firmly connected to milling head 12b and serves at the same time as guide element corresponding with guide bolt 30 of FIG. 4. To allow use of bone milling tool 10b, initially a continuous guide bore has to be established in the bone. For example, to shape a hip joint head by milling, the continuous guide bore is introduced through the shank neck. Driveshaft 14 is pushed from the direction of the shank head through the guide bore and on exit from the bone at the lateral side connected to a drive unit (not illustrated).

In the present bone milling tool 10b, guide bolts and driveshaft 14 coincide and toothing 20b is not arranged at the end surface but at the rear (similar to the lamellae of a mushroom), so that bone milling tool 10b does not operate by means of pushing on driveshaft 14 but by pulling the latter (see arrows 28). This makes it possible to also operate with a flexible driveshaft 14.

When working with a flexible driveshaft, it is of advantage to line the guide bore laterally with a guide pipe (not illustrated), so that rotary driveshaft 14 does not rub against the bone or adjacent soft parts. When working downwards, milling head 12b simply pushes the guide pipe ahead of itself without milling it.

Figure 2:
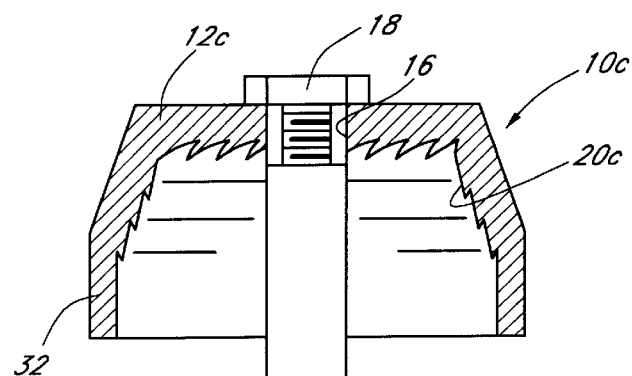
FIG. 2 a cross-sectional illustration of a further form of embodiment of the inventive bone milling tool with domeshaped cutting surface and screw connection between milling head and driveshaft.

FIG. 2 illustrates a further exemplary embodiment of a bone milling tool 10c, and the same reference numbers correspond with identical parts. Bone milling tool 10c differs from the one of FIG. 1 in two ways.

For one, milling head 12c is of domeshaped design as can be seen in the cross-sectional illustration. A concave cutting surface with respective toothing 20c is provided at the side of milling head 12c which is associated with driveshaft 14. This permits milling a shape surface which corresponds with said surface. The cutting surface is extended by a protruding, non-cutting protective collar 32 in order to keep soft parts away from the cutting zone.

Furthermore, driveshaft 14 and milling head 12c are detachably joined together, i.e. by means of a bolt 18. The latter is passed through a centered bore 16 in milling head 12c and is screwed into an inside thread at the side of the milling head of driveshaft 14. With a bone milling tool 10c of this type, driveshaft 14 is prior to a milling operation entered laterally from the end of the guide bore in the direction of the shank head and then connected to milling head 12c by means of bolt 18.

Figure 3:
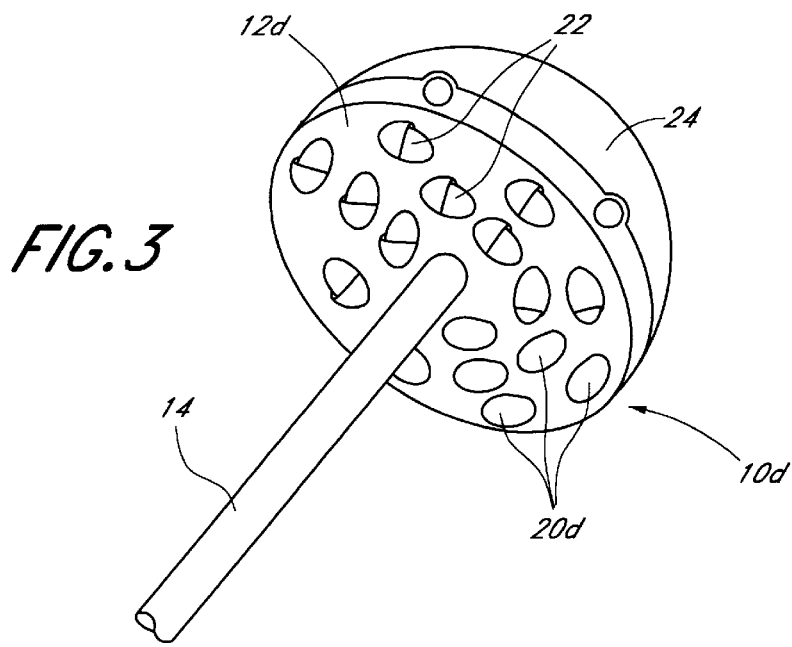
FIG. 3 a diagrammatical perspective illustration of a third form of embodiment of an inventive bone milling tool with rasplike toothing and collecting container.

A third embodiment of a bone milling tool 10d is illustrated in FIG. 3. This bone milling tool 10c offers special qualities relative to the aforedescribed forms of embodiment, in particular the one of FIG. 1. Toothing 20d at the driven surface of milling head 12d is of rasplike design and comprises waste removing holes 22 which extend through milling head 12d. Above the surface of milling head 12d opposite driveshaft 14 is arranged a removable collecting vessel 24, so that all bone waste severed by raspshaped toothing 20d and transported through waste remov ng holes 22 can be caught in said collecting vessel 24. This effectively prevents pollution of the field of operations thus limiting the danger of induced, undesirable ektopic bone growth. Bone waste caught in the removable collecting vessel 24 can subsequently be processed further into a valuable autologem spongiosa pulp.

In all, the described embodiments show bone milling tools by means of which a precisely fitting bone bed, for example for accommodating prostheses, can be created without elements of the bone milling tool protruding from the field of operation and making contact with objects in the field of operation. A directionally unstable or directionally incorrect milling surface can be effectively avoided.

Bone milling tools that are coated with hard material provide produce milled bone surfaces which distinguish themselves in that they bond completely with hydroxialpatit layered implant surface, for example within 10 and 14 days. This allows considerable acceleration in healing of implants.

Reference List 10a, b, c, d—Bone Milling Tool
12a, b, c, d—Milling Head
14—Driveshaft
14'—Driveshaft of the Prior Art
16—Bore
18—Bolt
20b, c, d—Toothing
22—Waste Removing Holes
24—Collecting Vessel
26—Arrow (symbolising Pushing Load)
28—Arrow (symbolising Pulling Load)
30—Guide Bolt
32—Protective Collar

What is claimed is:

1. A bone milling tool for precise preparation of bones, comprising:
    a milling head;
    a flexible driveshaft detachably connected to the milling head and configured to serve simultaneously as a guide element which is guided in a bone; and
    a toothing arranged on the milling head facing the driveshaft.

2. A bone milling tool for precise preparation of bones, comprising:
    a milling head;
    a flexible driveshaft connected to the milling head and configured to serve simultaneously as a guide element which is guided in a bone; and
    a toothing arranged on the milling head facing the driveshaft.

3. A bone milling tool for precise preparation of bones, comprising:
    a milling head;
    a driveshaft connected to the milling head and configured to serve simultaneously as a guide element which is guided in a bone;
    a guide pipe configured to be placed in the bone and to receive the driveshaft in a rotary mounted manner; and a toothing arranged on the milling head facing the driveshaft.

4. The bone milling tool of claim 1, wherein the driveshaft has a connection configured to detachably connect to a drive unit.

5. The bone milling tool of claim 1, wherein the milling head is symmetrical about an axis of rotation.

6. The bone milling tool of claim 5, wherein the milling head comprises a cutting surface having a shape selected from a group including essentially plane, concave, convex, and a combination of concave, convex and plane surfaces, and wherein said shape is prefixed.

7. A bone milling tool for precise preparation of bones, comprising:

a milling head, wherein the milling head comprises a cutting surface having a shape selected from a group including essentially plane, concave, convex, and a combination of concave, convex and plane surfaces, a non-cutting protective collar which protrudes over the milling head;

a driveshaft connected to the milling head and configured to serve simultaneously as a guide element which is guided in a bone; and a toothing arranged on the milling head facing the driveshaft.

8. The bone milling tool of claim 1, wherein the toothing of the milling head is milled or hammered.

9. A bone milling tool for precise preparation of bones, comprising:

a milling head;

a driveshaft connected to the milling head and configured to serve simultaneously as a guide element which is guided in a bone; and a toothing arranged on the milling head facing the driveshaft, wherein said toothing is rasplike with holes for the passage of milled bone.

10. The bone milling tool of claim 9, further comprising a collecting device detachably arranged on the milling head to collect bone waste which passes through the holes.

11. The bone milling tool of claim 10, wherein the collecting device is configured as a collecting vessel.

12. The bone milling tool of claim 11, wherein the collecting device is configured as a basket.

13. The bone milling tool of claim 6, wherein the cutting surface of the milling toothing are coated with a hard material.

14. The bone milling tool of claim 13, wherein the hard material is selected from a group including diamond, carbide and nitride.

* * * * *